US00PP36775P2

(12) United States Plant Patent
Winslow

(10) Patent No.: US PP36,775 P2
(45) Date of Patent: Jun. 24, 2025

(54) ***LOBELIA* PLANT NAMED 'WNLOBLRA26'**

(50) Latin Name: *Lobelia erinus*
Varietal Denomination: WNLOBLRA26

(71) Applicant: Benjamin K. Winslow, Austin, TX (US)

(72) Inventor: Benjamin K. Winslow, Austin, TX (US)

(73) Assignee: WINGEN, LLC, Mustang Ridge, TX (US)

( * ) Notice: Subject to any disclaimer, the term of this patent is extended or adjusted under 35 U.S.C. 154(b) by 0 days.

(21) Appl. No.: 18/956,442

(22) Filed: Nov. 22, 2024

(51) Int. Cl.
*A01H 5/02* (2018.01)
*A01H 6/26* (2018.01)

(52) U.S. Cl.
USPC ..... Plt./451
CPC ..... *A01H 6/268* (2018.05)

(58) Field of Classification Search
USPC ..... Plt./451
CPC ..... A01H 6/268; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Lobelia* plant named 'WNLOBLRA26', characterized by its relatively compact, upright to outwardly spreading and mounding to eventually trailing plant habit; vigorous and sturdy growth habit; freely branching habit; dense and bushy plant form; freely flowering habit; long flowering period; relatively large purplish blue-colored flowers with small white-colored centers; relative tolerance to high temperatures; and good container and garden performance.

2 Drawing Sheets

Figure 1:
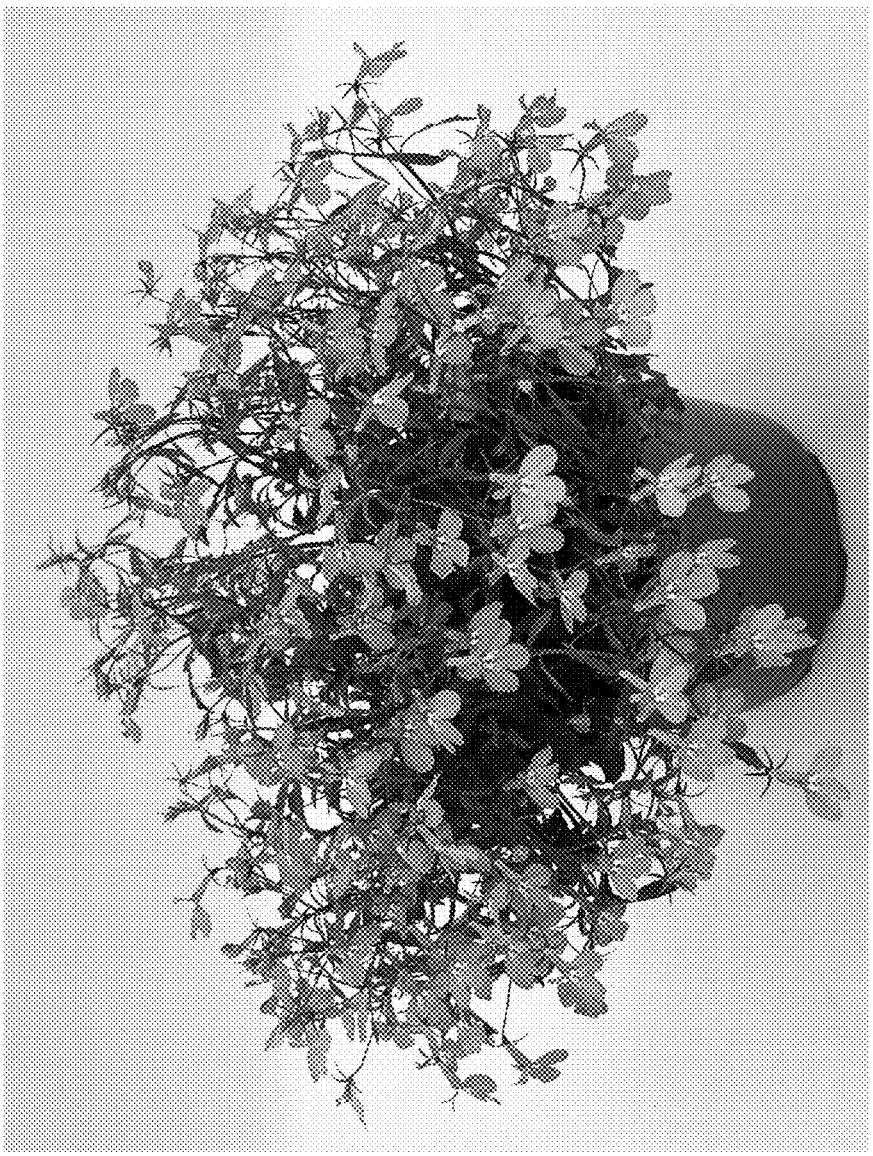

Botanical designation: *Lobelia erinus.*
Cultivar denomination: 'WNLOBLRA26'.

BACKGROUND OF THE INVENTION

The present invention relates to a new and distinct cultivar of *Lobelia* plant, botanically known as *Lobelia erinus* and hereinafter referred to by the name 'WNLOBLRA26'.

The new *Lobelia* plant is a product of a planned breeding program conducted by the Inventor in Alajuela, Costa Rica and Jacksonville, Texas. The objective of the breeding program is to create new outwardly spreading and freely-branching *Lobelia* plants with a long flowering period, high temperature tolerance and good garden performance.

The new *Lobelia* plant originated from a cross-pollination made by the Inventor in Alajuela, Costa Rica in October, 2019 of *Lobelia erinus* 'Weslowatim', not patented, as the female, or seed, parent with a proprietary selection of *Lobelia erinus* identified as code number LOB-0121-01, not patented, as the male, or pollen, parent. The new *Lobelia* plant was discovered and selected by the Inventor as a single flowering plant within the progeny of the stated cross-pollination in a controlled greenhouse environment in Jacksonville, Texas on Jan. 4, 2021.

Asexual reproduction of the *Lobelia* plant by vegetative terminal cuttings in Jacksonville, Texas since Jan. 21, 2021 has shown that the unique features of this new *Lobelia* plant are stable and reproduced true to type in successive generations.

SUMMARY OF THE INVENTION

Plants of the new *Lobelia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WNLOBLRA26'. These characteristics in combination distinguish 'WNLOBLRA26' as a new and distinct *Lobelia* plant:

1. Relatively compact, upright to outwardly spreading and mounding to eventually trailing plant habit.
2. Vigorous and sturdy growth habit.
3. Freely branching habit; dense and bushy plant form.
4. Freely flowering habit.
5. Long flowering period.
6. Relatively large purplish blue-colored flowers with small white-colored centers.
7. Relatively tolerant to high temperatures.
8. Good container and garden performance.

Plants of the new *Lobelia* differ primarily from plants of the female parent, 'Weslowatim', in the following characteristics:

1. Plants of the new *Lobelia* are more compact than plants of 'Weslowatim'.
2. Plants of the new *Lobelia* have lighter purplish blue-colored flowers than plants of 'Weslowatim'.
3. White-colored flower centers of plants of the new *Lobelia* are more pronounced than white-colored flower centers of plants of 'Weslowatim'.
4. Plants of the new *Lobelia* are more high temperature tolerant than plants of 'Weslowatim'.

Plants of the new *Lobelia* differ primarily from plants of the male parent selection in the following characteristics:

1. Plants of the new *Lobelia* are more compact than plants of the male parent selection.

2. Plants of the new *Lobelia* are more upright than and not as outwardly spreading as plants of the male parent selection.

Plants of the new *Lobelia* can be compared to plants of *Lobelia* x *hybrida* 'WNLOBLCBE23', disclosed in U.S. Plant patent application Ser. No. 18/135,166. In side-by-side comparisons, plants of the new *Lobelia* differ primarily from plants of 'WNLOBLCBE23' in flower color as flowers of plants of the new *Lobelia* are lighter purplish blue in color than flowers of plants of 'WNLOBLCBE23'. In addition, white-colored flower centers of plants of the new *Lobelia* are smaller than the white-colored flower centers of plants of 'WNLOBLCBE23'.

BRIEF DESCRIPTION OF THE PHOTOGRAPHS

The accompanying colored photographs illustrate the overall appearance of the new *Lobelia* plant showing the colors as true as it is reasonably possible to obtain in colored reproductions of this type. Colors in the photographs may differ slightly from the color values cited in the detailed botanical description which accurately describe the actual colors of the new *Lobelia* plant.

The photograph on the first sheet (FIG. 1) is a side perspective view of a typical flowering plant of 'WNLOBLRA26' grown in a container.

Figure 2:
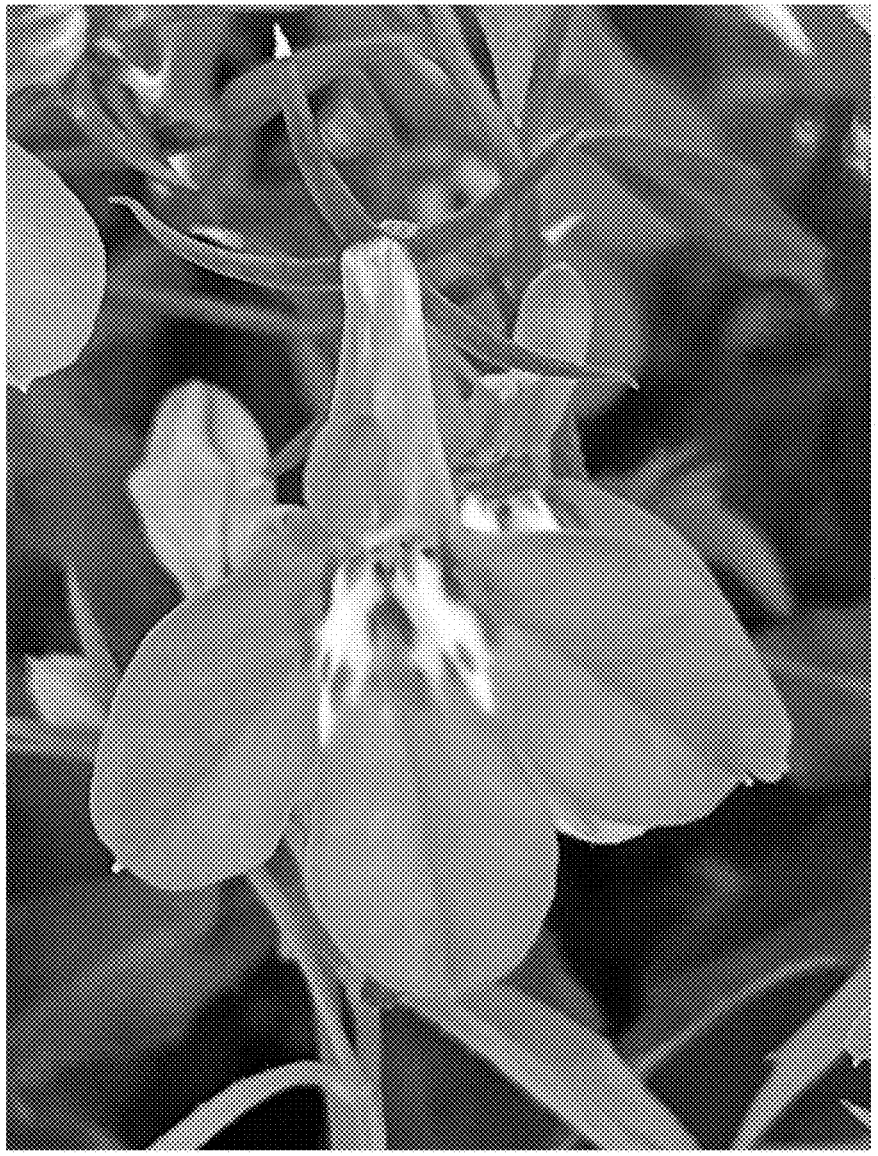

The photograph on the second sheet (FIG. 2) is a close-up view of a typical flowering plant of 'WNLOBLRA26'.

DETAILED BOTANICAL DESCRIPTION

The aforementioned photographs and following observations and measurements describe plants grown during the late summer to early autumn in 813 ml containers in a glass-covered greenhouse in Loudon, New Hampshire and under cultural practices typical of commercial *Lobelia* production. During the production of the plants, day temperatures ranged from 18° C. to 20° C. and night temperatures ranged from 16° C. to 18° C. Plants were pinched one time and were eight weeks from planting rooted young plants when the photographs and description were taken. In the following description, color references are made to The Royal Horticultural Society Colour Chart, 2015 Edition, except where general terms of ordinary dictionary significance are used.

Botanical classification: *Lobelia erinus* 'WNLOBLRA26'.

Parentage:

*Female, or seed, parent.*—*Lobelia erinus* 'Weslowatim', not patented.

*Male, or pollen, parent.*—Proprietary selection of *Lobelia erinus* identified as code number LOB-0121-01, not patented.

Propagation:

*Type cutting.*—Vegetative terminal cuttings.

*Time to initiate roots, summer.*—About seven to twelve days at ambient temperatures about 28° C.

*Time to initiate roots, winter.*—About 10 to 14 days at ambient temperatures about 20° C.

*Time to produce a rooted young plant, summer.*—About three to four weeks at ambient temperatures about 28° C.

*Time to produce a rooted young plant, winter.*—About four to five weeks at ambient temperatures about 20° C.

*Root description.*—Fine, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Relatively compact, upright to outwardly spreading and mounding to eventually trailing plant habit; freely branching habit with lateral branches developing at potentially every node; dense and bushy plant habit; vigorous and sturdy growth habit and moderate growth rate.

*Plant height.*—About 11 cm to 13 cm.

*Plant width.*—About 32 cm to 34 cm.

*Lateral branch description.*—Length: About 14 cm to 16 cm. Diameter: About 2 mm. Internode length: About 1.7 cm to 2 cm. Strength: Strong, flexible; wiry. Aspect: Upright to outwardly spreading to eventually trailing. Texture and luster: Smooth, glabrous; somewhat glossy. Color: Close to a blend of 144A and 146A.

Leaf description:

*Arrangement.*—Alternate, simple.

*Length.*—About 2.75 cm to 3 cm.

*Width.*—About 1.75 cm to 2 cm.

*Shape.*—Elliptic to obovate; slightly recurved and twisting.

*Apex.*—Acute.

*Base.*—Cuneate.

*Margin.*—Crenate; not undulate.

*Texture and luster, upper and lower surfaces.*—Smooth, glabrous; glossy.

*Venation pattern.*—Pinnate.

*Color.*—Developing leaves, upper and lower surfaces: Close to 146A. Fully expanded leaves, upper surface: Close to between 146A and 147A; venation, close to between 146A and 147A. Fully expanded leaves, lower surface: Close to 146A variably tinged with close to 59A; venation, close to 146A.

*Petioles.*—Length: About 6 mm to 8 mm. Diameter: About 2 mm. Texture and luster: Smooth, glabrous; somewhat glossy. Color, upper surface: Close to between 146A and 147A. Color, lower surface: Close to 146A.

Flower description:

*Flower arrangement, habit and shape.*—Single, flowers axillary or terminal; flowers face mostly outwardly; freely flowering habit with flowers potentially developing at every axil; flowers bilabiate with two small upper petals and three larger fused lower petals.

*Fragrance.*—None detected.

*Natural flowering season.*—Long flowering period, in New Hampshire, plants of the new *Lobelia* flower continuously from planting in the spring until frost in the autumn; early flowering habit, plants begin flowering about seven to eight weeks after planting rooted young plants.

*Flower longevity on the plant.*—Longevity of individual flowers is highly dependent on temperature, flowers typically last about one to two weeks on the plant; flowers persistent.

*Flower height.*—About 1.75 cm.

*Flower width.*—About 2 cm.

*Flower depth.*—About 1.75 cm to 2 cm.

*Flower throat diameter.*—About 4 mm.

*Flower tube length*.—About 1 cm.

*Flower tube diameter, distally*.—About 4 mm.

*Flower tube diameter, proximally*.—About 2 mm.

*Flower buds*.—Length: About 1.2 cm. Diameter: About 4 mm. Shape: Oblong to obovate. Color, developing sepals: Close to 144A to 144B.

*Petals*.—Arrangement: Single whorl of five petals fused towards the base; two small upper petals and three larger fused lower petals. Lower petals: Lobe length, beyond throat: About 1.2 cm. Lobe width, beyond throat: About 6 mm to 8 mm. Shape: Oblanceolate to obovate. Apex: Cuspidate. Margin: Entire; not undulate. Texture and luster, upper and lower surfaces: Smooth, glabrous; matte. Color, when opening and fully opened, upper surface: Close to between 95C and 96B to 96C; towards the throat, close to NN155D with spots, close to 96A to 96B; venation, similar to lamina colors; main color becoming closer to 96C to 96D with subsequent development and eventually, closer to 97B to 97C. Color, when opening and fully opened, lower surface: Close to between 95D and 97B; venation, similar to lamina color; color becoming closer to 97C to 97D with subsequent development. Upper petals: Lobe length, beyond throat: About 9 mm to 10 mm. Lobe width, beyond throat: About 2.5 mm to 3 mm. Shape: Oblong. Apex: Cuspidate. Margin: Entire; not undulate. Texture and luster, upper and lower surfaces: Smooth, glabrous; matte. Color, when opening and fully opened, upper surface: Close to between 95C and 96B to 96C; venation, similar to lamina color; color becoming closer to 96C to 96D with subsequent development and eventually, closer to 97B to 97C. Color, when opening and fully opened, lower surface: Close to 96B to 96C; venation, similar to lamina color; color becoming closer to 97B to 97C with subsequent development. Color, throat: Close to 97C; spots, close to 96A; nectar guides, close to 154D. Color, tube: Close to 97A to 97B.

*Sepals*.—Arrangement: Single whorl of five sepals, fused at the base; star-shaped calyx. Length: About 7.5 mm. Width: About 1 mm. Shape: Acicular. Apex: Acute. Margin: Entire; not undulate. Texture and luster, upper and lower surfaces: Smooth, glabrous; slightly glossy. Color, upper and lower surfaces: Close to between 146A and 147A.

*Peduncles*.—Length: About 1.75 cm. Diameter: Less than 1 mm. Strength: Strong, flexible; wiry. Aspect: About 45° from the lateral branch axis. Texture and luster: Smooth, glabrous; slightly glossy. Color: Close to 146A.

*Reproductive organs*.—Stamens: To date, stamen development has not been observed on plants of the new *Lobelia*. Pistils: Quantity per flower: One. Pistil length: About 9 mm to 10 mm. Stigma shape: Blunt. Stigma color: Close to N187A. Style color: Close to 144A to 144B tinged with close to N187A. Ovary color: Close to between 144A and 146A.

*Fruits and seeds*.—To date, fruit and seed development have not been observed on plants of the new *Lobelia*.

Pathogen & pest resistance: To date, plants of the new *Lobelia* have not been noted to be resistant to pathogens and pests common to *Lobelia* plants.

Garden performance: Plants of the new *Lobelia* have been observed to have good garden performance and to tolerate wind, rain and to be tolerant to high temperatures of about 40° C.

It is claimed:

1. A new and distinct *Lobelia* plant named 'WNLOBLRA26' as herein illustrated and described.

* * * * *